United States Patent
Weng et al.

(10) Patent No.: US 9,485,846 B2
(45) Date of Patent: Nov. 1, 2016

(54) METHOD AND SYSTEM FOR INSPECTING AN EUV MASK

(71) Applicant: Hermes Microvision Inc., Hsinchu (TW)

(72) Inventors: Guochong Weng, San Jose, CA (US); Youjin Wang, San Jose, CA (US); Chiyan Kuan, San Jose, CA (US); Chung-Shih Pan, San Jose, CA (US)

(73) Assignee: HERMES MICROVISION INC., Hsinchu (TW)

(*) Notice: Subject to any disclaimer, the term of this patent is extended or adjusted under 35 U.S.C. 154(b) by 0 days.

(21) Appl. No.: 14/575,102

(22) Filed: Dec. 18, 2014

(65) Prior Publication Data
US 2015/0102220 A1    Apr. 16, 2015

Related U.S. Application Data

(63) Continuation-in-part of application No. 14/039,939, filed on Sep. 27, 2013, now Pat. No. 9,113,538, which is a continuation-in-part of application No. 13/112,536, filed on May 20, 2011, now Pat. No. 8,575,573.

(51) Int. Cl.
| | | |
|---|---|---|
| *G01N 23/00* | (2006.01) | |
| *H05F 3/02* | (2006.01) | |
| *H01J 37/20* | (2006.01) | |
| *G01N 23/225* | (2006.01) | |
| *H01J 37/02* | (2006.01) | |

(52) U.S. Cl.
CPC ............ *H05F 3/02* (2013.01); *G01N 23/2251* (2013.01); *H01J 37/026* (2013.01); *H01J 37/20* (2013.01); *H01J 2237/004* (2013.01); *H01J 2237/0041* (2013.01); *H01J 2237/0044* (2013.01); *H01J 2237/202* (2013.01); *H01J 2237/2007* (2013.01); *H01J 2237/2008* (2013.01); *H01J 2237/2811* (2013.01); *H01J 2237/2813* (2013.01)

(58) Field of Classification Search
None
See application file for complete search history.

(56) References Cited

U.S. PATENT DOCUMENTS

| | | | |
|---|---|---|---|
| 4,610,020 A | 9/1986 | La Fiandra | |
| 5,608,773 A | 3/1997 | Korenaga et al. | |
| 5,665,968 A * | 9/1997 | Meisburger | H01J 37/28 250/306 |
| 5,671,123 A | 9/1997 | Omori et al. | |
| 6,172,738 B1 | 1/2001 | Korenaga et al. | |
| 6,906,305 B2 * | 6/2005 | Pease | G03F 7/70591 250/208.1 |
| 7,834,982 B2 | 11/2010 | Yamamoto | |
| 8,575,573 B2 * | 11/2013 | Wang | H01J 37/026 250/310 |
| 2001/0022652 A1 | 9/2001 | van Schaik et al. | |
| 2002/0047093 A1 * | 4/2002 | Son | G01N 23/04 250/307 |
| 2002/0070340 A1 * | 6/2002 | Veneklasen | H01J 37/256 250/310 |
| 2002/0075469 A1 * | 6/2002 | Tanaka | G03F 7/70716 355/72 |
| 2003/0162101 A1 * | 8/2003 | Heerens | G03F 7/70741 430/5 |
| 2005/0082476 A1 * | 4/2005 | Hiroi | H01J 37/28 250/310 |
| 2006/0292457 A1 * | 12/2006 | Meijer | B82Y 10/00 430/5 |
| 2007/0111342 A1 * | 5/2007 | Satya | H01L 22/34 438/17 |
| 2007/0117028 A1 | 5/2007 | Heerens et al. | |
| 2008/0149830 A1 * | 6/2008 | Baek | H01J 37/026 250/310 |
| 2009/0301917 A1 * | 12/2009 | Kolbow | G03F 1/66 206/454 |

* cited by examiner

*Primary Examiner* — Andrew Smyth
(74) *Attorney, Agent, or Firm* — WPAT, PC; Justin King; Jonathan Chiang

(57) ABSTRACT

A structure for grounding an extreme ultraviolet mask (EUV mask) is provided to discharge the EUV mask during the inspection by an electron beam inspection tool. The structure for grounding an EUV mask includes at least one grounding pin to contact conductive areas on the EUV mask, wherein the EUV mask may have further conductive layer on sidewalls or/and back side. The inspection quality of the EUV mask is enhanced by using the electron beam inspection system because the accumulated charging on the EUV mask is grounded. The reflective surface of the EUV mask on a continuously moving stage is scanned by using the electron beam simultaneously. The moving direction of the stage is perpendicular to the scanning direction of the electron beam.

4 Claims, 23 Drawing Sheets

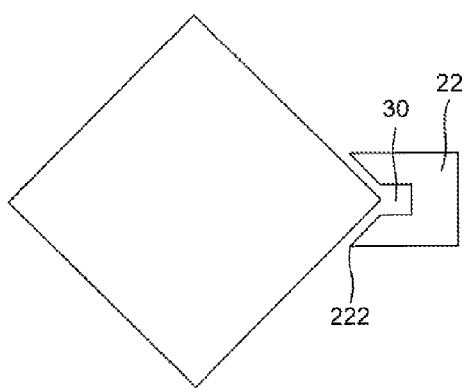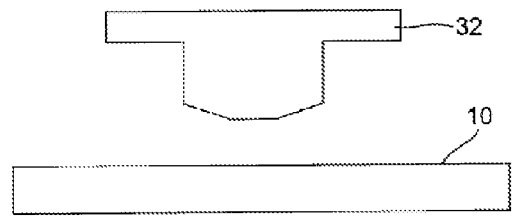
Fig.4
Fig.5

Slightly contacting a grounding pin to the EUV mask while the EUV mask is positioned;
S110

Continuously moving a stage, for supporting the EUV mask, and scanning the reflective surface of the EUV mask by using a charged particle beam simultaneously;
S120

Receiving signal electrons emanated from the reflective surface of the EUV mask.
S130

Figure 19

METHOD AND SYSTEM FOR INSPECTING AN EUV MASK

CLAIM OF PRIORITY

This application is a continuation-in-part of pending U.S. application Ser. No. 14/039,939 filed Sep. 27, 2013, which is a continuation of U.S. application Ser. No. 13/112,536 filed May 20, 2011, now U.S. Pat. No. 8,575,573 issued Nov. 5, 2013, the entire disclosures of which are incorporated herein by reference.

BACKGROUND OF THE INVENTION

1. Field of the Invention

The present invention relates to a method for inspecting an EUV mask by using a charged particle beam, and more especially, to a method for inspecting the EUV mask with grounding means such that the EUV mask can be continuous scanned by electron beams.

2. Background of the Related Art

Optical inspection of a mask is based on a comparison of the light signals in the patterned regions relative to the non-patterned regions. A high contrast is necessary in order to achieve sufficient sensitivity for defect detection. The transmissive masks used in DUV (deep Ultra Violet) lithography can be inspected without difficulty since the contrast between the opaque regions and the clear regions is high at UV/DUV wavelengths. However, it is difficult to inspect the reflective masks, the EUV mask for example, used in EUV lithography since not only the contrast between the absorber region and the mirror region is low at UV/DUV wavelengths, but also wavelength of the UV/DUV is too lengthy to inspect EUV mask.

Now, a charged particle beam inspection system, an electron beam (E-beam) inspection tool, accordingly, is developed to inspect the EUV mask. However, accumulated charging on EUV mask will induce inspection issue while the EUV mask is inspected by the E-beam inspection tool. This issue will not happen to silicon wafer because silicon wafer can be grounded. Substrate of the EUV mask is dielectric, and cannot be grounded.

Furthermore, if the EUV mask on a moving stage is scanned continuously by the electron beam and charges are accumulated on the surface of the EUV mask without grounding, the contrast and intensity of the scanned images at different areas would not be consistent or equal during the inspection process. In other words, the electron beam scanning over different regions of the EUV mask would cause dwell times in order to make the images have better quality and consistent contrast and intensity during the inspection operation. The inspection speed and the throughput would be influenced greatly.

SUMMARY OF THE INVENTION

In order to solve the foregoing problems, one object of this invention is to provide a structure to discharge the EUV mask during inspection by an E-beam inspection tool, so that non accumulated charging is on the EUV mask during E-beam inspecting to enhance the inspection quality.

Accordingly, one embodiment of the present invention provides a structure for discharging EUV mask including: means for conducting charge on an EUV mask in inspecting the EUV mask by using a charged particle beam inspection system; and a grounding pin to contact the means.

Another embodiment of the present invention provides a structure for discharging EUV mask including: at least a conductive layer on one side of an EUV mask; and a grounding pin to contact the conductive layer, so that charge on a reflective surface of the EUV mask is grounded through the conductive layer to the grounding pin.

Another embodiment of the present invention provides a structure for discharging EUV mask including: a first conductive layer on one side of an EUV mask; a second conductive layer on a surface opposite to a reflective surface of the EUV mask; and a grounding pin to contact the second conductive layer, so that charge on the reflective surface of the EUV mask is grounded through the second conductive layer to the grounding pin.

Another embodiment of the present invention provides an electron beam inspection system for inspecting an EUV mask including: an electron gun for providing electron beam; a lens for focusing the electron beam on the EUV mask; a detector for receiving signal electron emanating from the EUV mask; and means for discharging the EUV mask during the EUV mask is inspected.

Another embodiment of the present invention provides a method for inspecting an EUV mask by using a charged particle beam including: grounding the EUV mask; moving a stage, for supporting the EUV mask, continuously and scanning a surface of the EUV mask by using the charged particle beam simultaneously; and receiving signal electrons emanated from the surface of the EUV mask.

Another embodiment of the present invention provides a system for inspecting an EUV mask including: a source for providing an electron beam; an objective lens for focusing the electron beam on a surface of the EUV mask; a detector for receiving signal electrons emanated from the surface of the EUV mask; a stage for supporting the EUV mask; and means for grounding the EUV mask, wherein the surface of the EUV mask is scanned by the electron beam when the stage moves continuously, Another embodiment of the present invention provides a method for inspecting an EUV mask by using a charged particle beam, which comprises steps of grounding the EUV mask, moving a stage continuously and scanning a reflective surface of the EUV mask by using the charged particle beam simultaneously, and receiving signal electrons emanated from the surface of the EUV mask, wherein the stage supports the EUV mask.

The charged particle beam can be an electron beam. A stage's moving direction is perpendicular to a scanning direction of the electron beam. The EUV mask can be inspected by a low voltage scanning electron microscope. The step of grounding the EUV mask can be performed by slightly contacting a grounding pin to the reflective surface of the EUV mask.

The step of grounding the EUV mask can be performed by contacting a grounding pin to a back surface of the EUV mask and electrically connecting to the reflective surface of the EUV mask. The grounding pin can contact the back surface of the EUV mask slightly.

The step of grounding the EUV mask can be performed by slightly contacting a grounding pin to a conductive layer on one side wall of the EUV mask. A trench can be formed in the side wall of the EUV mask. The conductive layer can be coated within the trench.

Another embodiment of the present invention provides a system for inspecting an EUV mask, which comprises a source for providing an electron beam, an objective lens for focusing the electron beam on a reflective surface of the EUV mask, a detector for receiving signal electrons emanated from the surface of the EUV mask, a stage for supporting the EUV mask, and means for grounding the EUV mask, wherein the surface of the EUV mask is scanned by the electron beam when the stage moves continuously.

A stage's moving direction is perpendicular to a scanning direction of the electron beam. The system can be a low voltage scanning electron microscope. The means for grounding the EUV mask can include a grounding pin slightly contacting the reflective surface of the EUV mask.

The means for grounding the EUV mask can include a grounding pin contacting a back surface of the EUV mask, and a conductive layer can be on the back surface of the EUV mask and electrically connecting to the reflective surface of the EUV mask. The grounding pin can contact the back surface of the EUV mask slightly.

The means for grounding the EUV mask can include a grounding pin contacting a conductive layer on one side wall of the EUV mask. A trench can be formed in the side wall of the EUV mask. The conductive layer can be coated within the trench.

BRIEF DESCRIPTION OF THE DRAWINGS

FIG. 4 illustrates a diagram about a configuration of the EUV mask and the slider;

FIG. 5 illustrates a diagram about a configuration of the EUV mask and the electron gun;

FIG. 19 is a flow chart illustrating a method for inspecting an EUV mask by using a charged particle beam in accordance with one embodiment of the present invention.

DETAILED DESCRIPTION OF THE INVENTION

Figure 1:
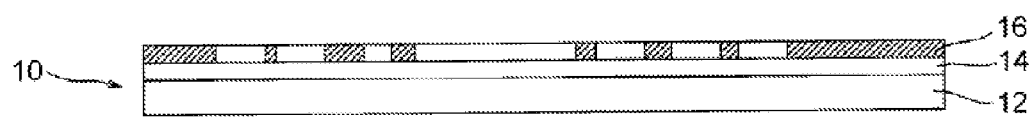
FIG. 1 illustrates a cross-sectional view of a configuration of an EUV mask.
Figure 2:
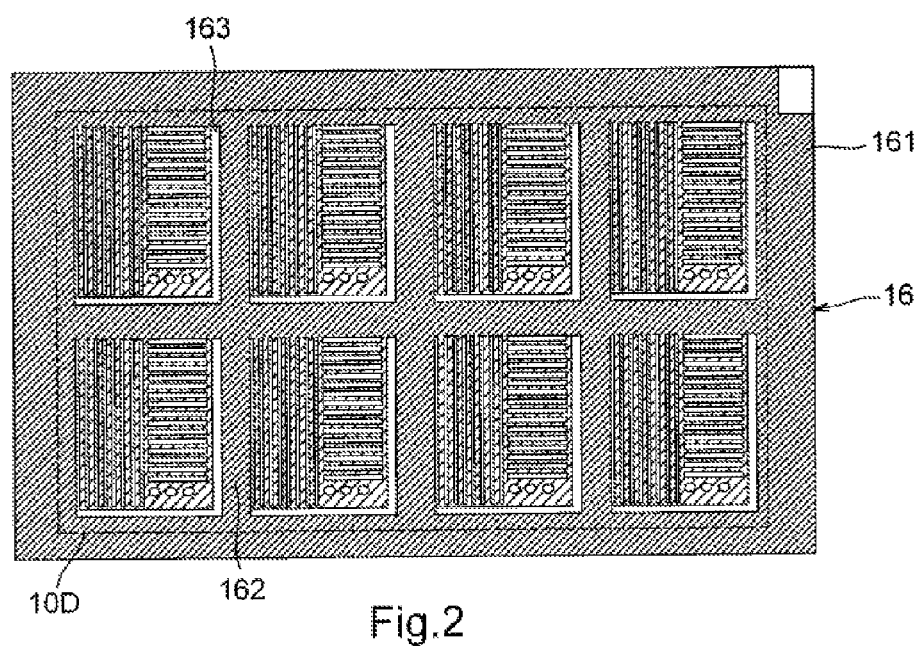
FIG. 2 illustrates a vertical view of a configuration of an EUV mask.

FIG. 1 illustrates a cross-sectional view of a configuration of an EUV mask. The EUV mask 10 includes a substrate 12, an EUV absorption layer 14 on the substrate 12 and a patterned reflective surface 16 formed on the absorption layer 14. Referring to FIG. 2 simultaneously, the patterned reflective surface 16 has a peripheral area 161 without any pattern and a middle area 162 with a plurality of pattern openings 163 thereon. Here, the patterned reflective surface of the EUV mask may be holes, circuits, devices, or any combination thereof. In one embodiment, the reflective layer, made of the same or different metals, is formed on a substrate of the EUV mask, and portion of the plurality of patterns may distribute on the reflective layer. A structure for discharging EUV mask includes: means for conducting charge on the EUV mask 10 in inspecting the EUV mask 10 by using a charged particle beam inspection system; and a grounding pin (shown in following diagrams) to contact the means. In one embodiment, the grounding pin is used to contact a portion of the peripheral area 161 of the patterned reflective surface 16, which is made of electrical conductive materials, or electrical semiconductive materials, and thereby grounds charges on the reflective surface 16 of the EUV mask 10.

Figure 3A:
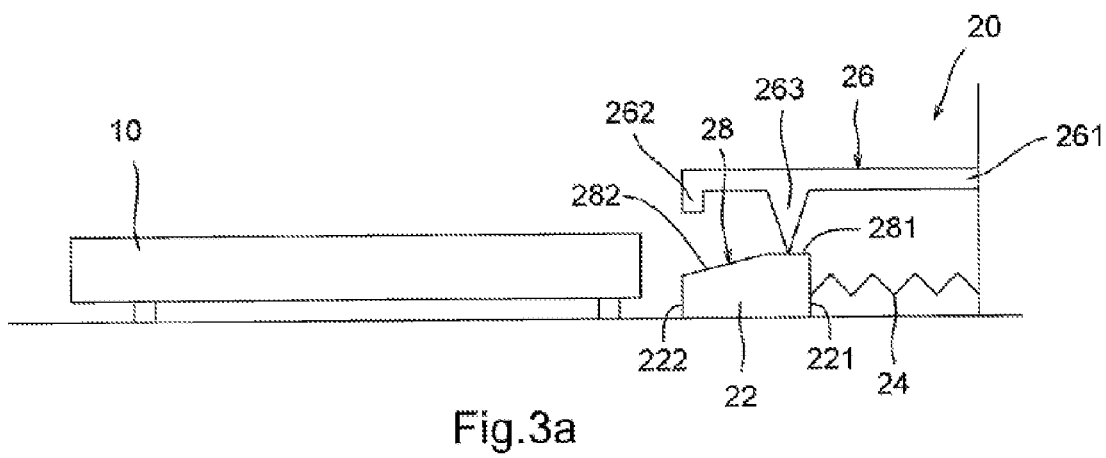
FIG. 3a and FIG. 3b illustrate the diagrams about the working status of the EUV mask and the grounding pin in accordance with the first embodiment of the present invention.
Figure 3B:
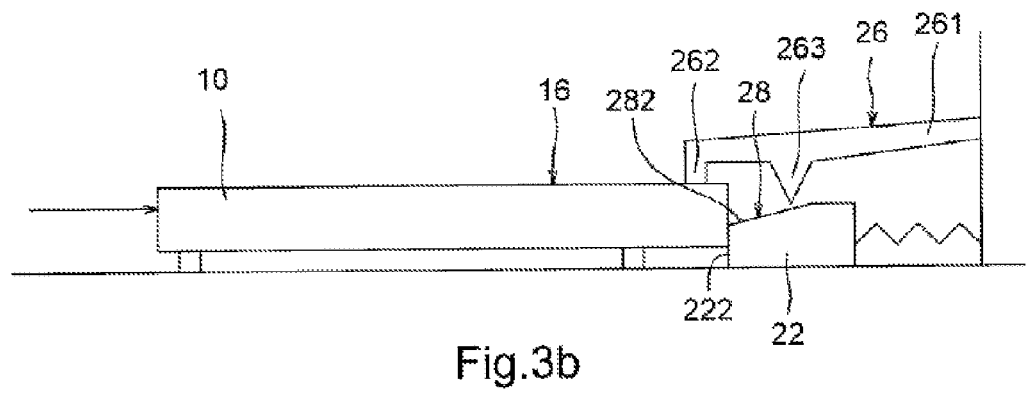

FIG. 3a and FIG. 3b illustrate the diagrams about the working of the EUV mask and the grounding pin in accordance with the first embodiment of the present invention. In the first embodiment, the structure 20 for discharging EUV mask further includes a slider 22, a spring 24 and an arm structure 26. The slider 22 has a top surface 28 divided into a flat area 281 and a downward-tilted area 282. One end of the spring 24 connects to a back side 221 of the slider 22 and the other end of the spring 24 is fixed. The arm structure 26 is above the slider 22 and the arm structure 26 includes a body 261, the grounding pin 262 on a front end of the body 261 and a prop 263 connecting to the body 261. As shown in FIG. 3a, when the EUV mask 10 is under the ungrounded status, the prop 263 of the arm structure 26 contact the flat area 281 of the slider 22 and the grounding pin 262 is far away from the EUV mask 10. When the EUV mask 10 moves toward a front side 222 of the slider 22 to contact and push the slider 22 back, as shown in FIG. 3b, the prop 263 moves along the top surface 28 of the slider 22 and then contacts the downward-tilted area 282, and therefore the body 261 of the arm structure 26 tilts and the grounding pin 262 contacts the reflective surface 16 of the EUV mask 10.

As shown in FIG. 4, the slider 22 has a gap 30 on the front side 222 of the slider 22 for holding one corner of the EUV mask 10, so that the slider 22 may fix the EUV mask 10, as the EUV mask 10 contacts with the slider 22 during the EUV mask 10 is grounded by the grounding pin 262 (shown in FIG. 3a, FIG. 3b) and inspected by charged particle beam inspection system, in which the electron gun 32 for providing electron beam is above the EUV mask 10, as shown in FIG. 5.

Figure 6A:
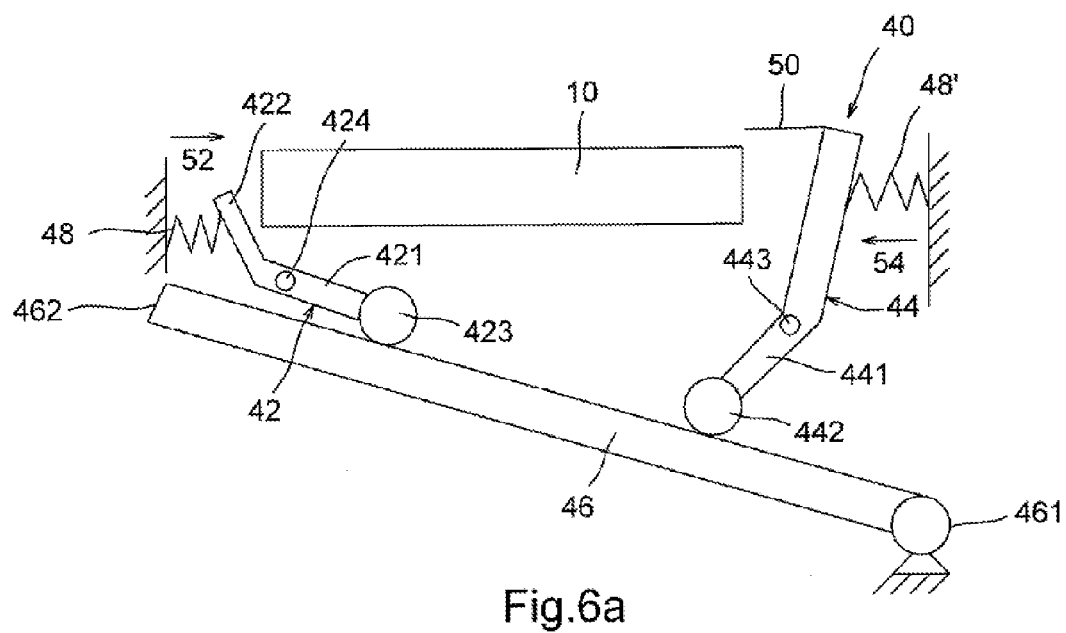
FIG. 6a and FIG. 6b illustrate the diagrams about the working status of the EUV mask and the grounding pin in accordance with the second embodiment of the present invention.
Figure 6B:
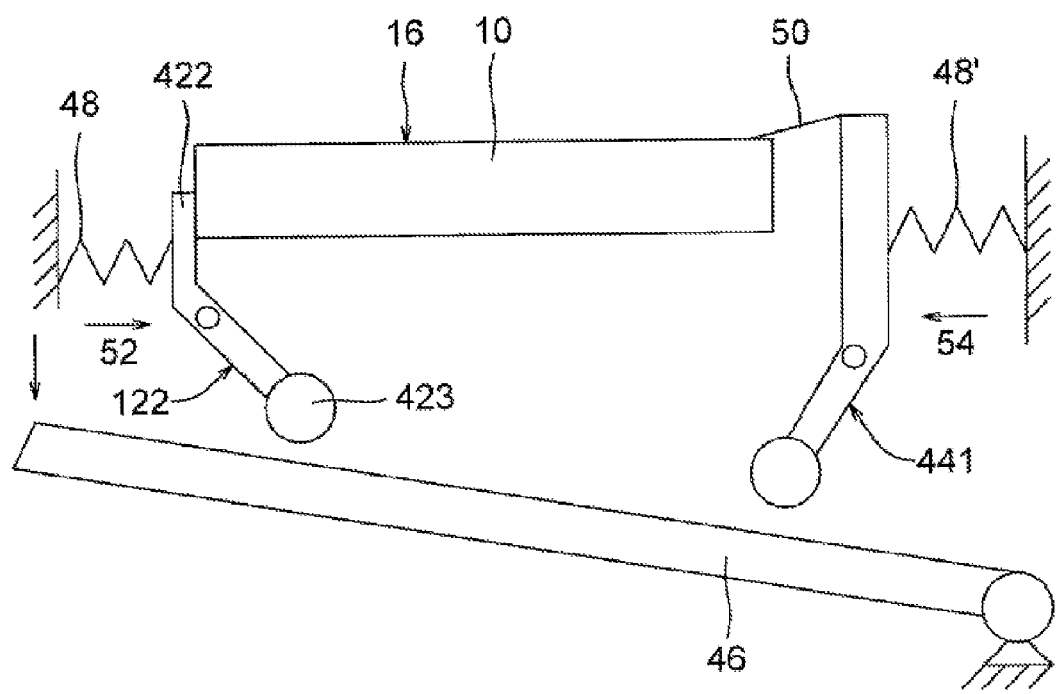

FIG. 6a and FIG. 6b illustrate the diagrams about the working status of the EUV mask and the grounding pin in accordance with the second embodiment of the present invention. In the second embodiment, as shown in FIG. 6a and FIG. 6b, the structure 40 for discharging EUV mask further includes a gripper unit 42, an arm structure 44, a reciprocating member 46 and two resilient members 48, 48'.

The gripper unit 42 includes a head portion 421, a base portion 422 and a first rolling member 423 set at a bottom end of the base portion 421. The gripper unit 42 is used for fixing the EUV mask 10 in place, for example but not limited to, being held tight or to be released, through rotation of the gripper unit 42 about a first pivot 424 substantially parallel with a first center axis of the first rolling member 423.

The arm structure 44 is configured near or opposite the gripper unit 42. The arm structure 44 includes a body 441, the grounding pin 50 on a top end of the body 441 and a second rolling member 442 set at a bottom end of the body 441. The grounding pin 50 may reciprocate to contact the EUV mask 10 and leave the EUV mask 10 through rotation of the body 441 about a second pivot 443 substantially parallel with a second center axis of the second rolling member 442.

The two resilient members are one first resilient member 48 and one second resilient member 48' each with one end being fixed, and respectively with the other ends being connected to head portion 422 of the gripper unit 42 and to the body 441 of the arm structure 44 for respectively providing a first force to the gripper unit 42 toward a first direction 52 and a second force to the body 441 of the arm structure 44 toward a second direction 54.

The reciprocating member 46 is configured for causing the first rolling member 423 and the second rolling member 442 to rotate. The reciprocating member 46 includes a fix end 461 and a mobile end 462 pivoting the fixed end 461. The first rolling member 423 and the second rolling member 442 may be in contact with reciprocating member 46 and roll freely on the surface of the reciprocating member 46. Here, the reciprocating member 46 is tilted by pushing up and pulling down the mobile end 462 of the reciprocating member 46 pivoting the fixed end 461 of the reciprocating member 46, which results in the first rolling member 423 and the second rolling member 442 rolling on the reciprocating member 46.

As shown in FIG. 6a, when the reciprocating member 46 works to make the first rolling member 423 to move substantially along the first direction 52 and the second rolling member 442 move substantially along the second direction 54, the head portion 422 of the gripper unit 42 moves toward the opposite direction of the first direction 52 and the grounding pin 50 moves toward the opposite direction of the second direction 54 so that the head portion 422 and the grounding pin 50 are led away from the EUV mask 10. As shown in FIG. 6b, when the reciprocating member 46 works to leave the first rolling member 423 and the second rolling member 442, the head portion 422 of the gripper unit 42 moves toward the first direction 52 by means of the first force of the first resilient member 48 and an upper portion of the arm structure 44 moves toward the second direction 54 by means of the second force of the second resilient member 48', so that the head portion 422 is therefore led toward the edge of the EUV mask 10 and in the end to abut against the EUV mask 10, and the grounding pin 50 contacts the reflective surface 16 of the EUV mask 10. Here, the head portion 422 of the gripper unit 42 is used to push tighter against the EUV mask 10 to hold it fixed in position during the EUV mask 10 is grounded by the grounding pin 50 and inspected by the charged particle beam inspection system.

Figure 7A:
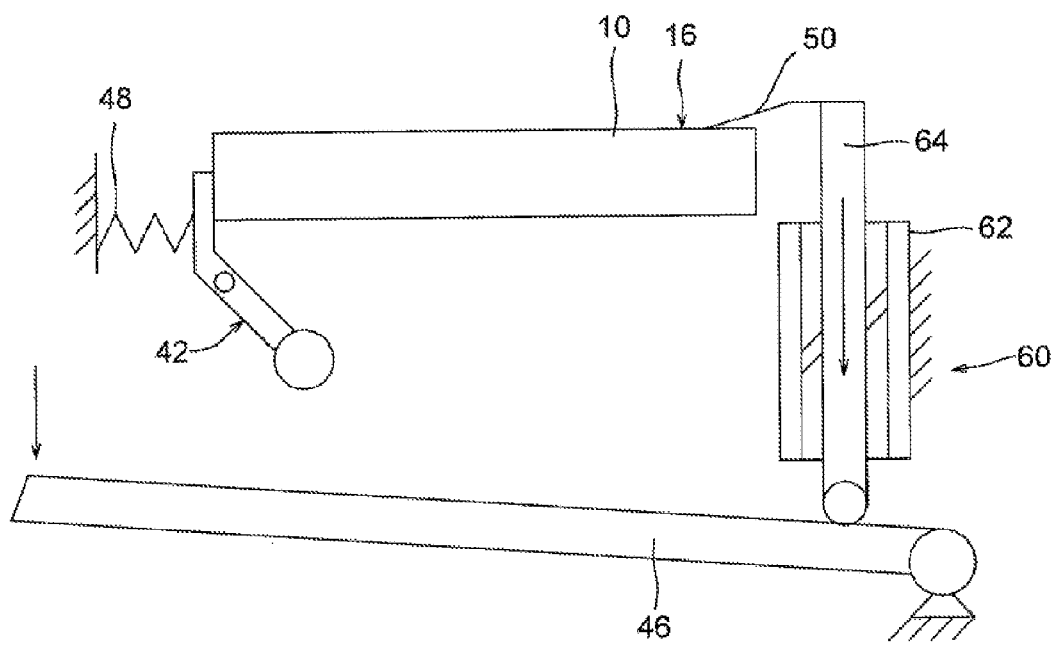
FIG. 7a and FIG. 7b illustrate the diagrams about the working status of the EUV mask and the grounding pin in accordance with the third embodiment of the present invention.
Figure 7B:
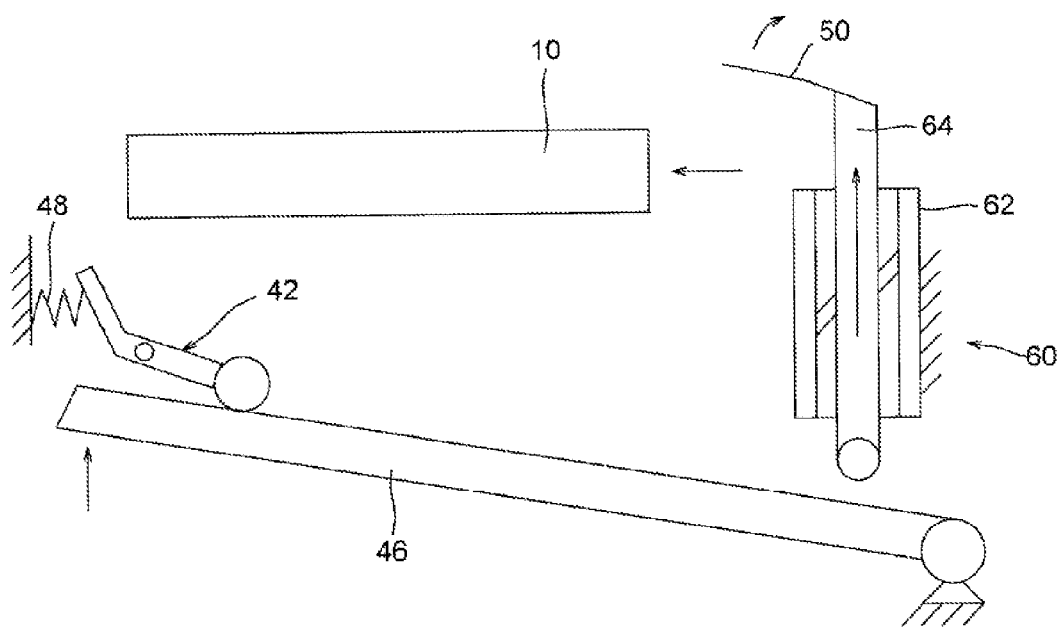

FIG. 7a and FIG. 7b illustrate the diagrams about the working status of the EUV mask and the grounding pin in accordance with the third embodiment of the present invention. In the third embodiment, the structure for discharging EUV mask further includes the foregoing gripper unit 42, the foregoing first resilient member 48, the foregoing reciprocating member 46 and a grounding pin controlling structure 60. Here, the structures, the connection relations and the operation of the gripper unit 42, the first resilient member 48 and the reciprocating member 46 are described in the second embodiment as shown in FIG. 6a and FIG. 6b, wherein the head portion 422 of the gripper unit 42 is used to push tighter against the EUV mask 10 to hold it fixed in position during the EUV mask 10 is grounded by the grounding pin 50. The grounding pin controlling structure 60 includes a hollow cylinder 62 and a column 64 passing through the hollow cylinder 62. A grounding pin 50 is arranged on a top surface of the column 64 and the position of the grounding pin 50 is changed by moving the column 64. As shown in FIG. 7a, when the gripper unit 42 pushes tighter against the EUV mask 10, the column 64 moves down and the grounding pin 50 contacts the reflective surface 16 of the EUV mask 10. As shown in FIG. 7b, when the gripper unit 42 releases the EUV mask 10, the column 62 moves up and the grounding pin 50 is far away from the EUV mask 10.

Figure 8:
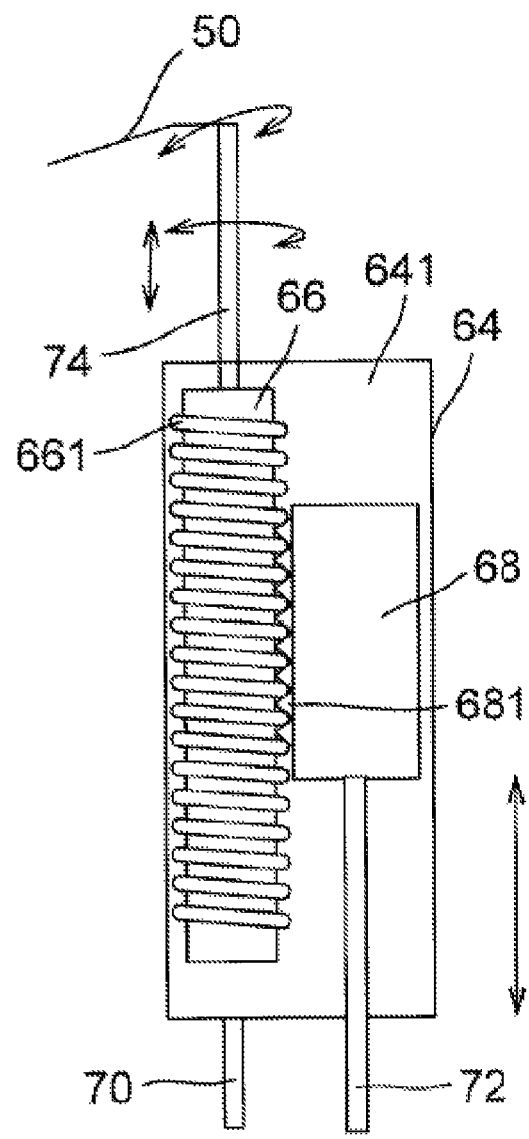
FIG. 8 illustrates a first embodiment of the grounding pin controlling structure.

In first embodiment of the grounding pin controlling structure, the grounding pin controlling structure 60 includes a hollow cylinder 62 and a column 64 passing through the hollow cylinder 62, wherein the column 64 has an interior room 641, as shown in FIG. 8. A first rod 66 with the spiral shells 661 on the outer surface and a second rod 68 with the sawtooth 681 on the outer surface are configured in the interior room 641, wherein the spiral shells 661 and the sawtooth 681 are engaged with each other. A first pushing shaft 70 is connected to the bottom of the column 64 and a second pushing shaft 72 is connected to the bottom of the second rod 68 and passes through the bottom of the column 64. One end of a connection rod 74 is connected to the top of the first rod 66, and another end of the connection rod 74 is connected with a grounding pin 50. During the inspection of the EUV mask 10, the column 64 moves down in relative to the hollow cylinder 62 (shown in FIG. 7a), so that the grounding pin 50 contacts the reflective surface 16 of the EUV mask 10 (shown in FIG. 7a). After the inspection of the EUV mask 10, the column 64 moves up continuously in relative to the hollow cylinder 62 (shown in FIG. 7b) so that the grounding pin 50 rise, wherein the second rod 72 also moves up to drive the first rod 66 to rotate with the sawtooth 681 engaging with the spiral shells 661, so that the grounding pin 50 may rise and deflect, simultaneously to be far away from the EUV mask.

Figure 9A:
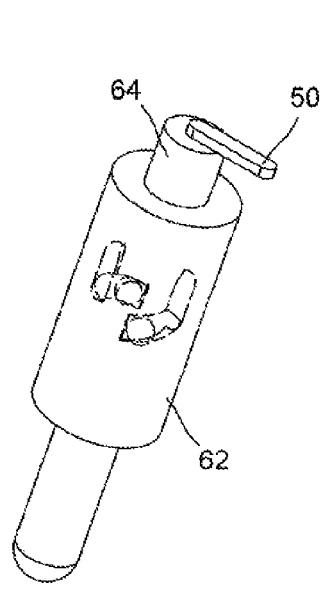
FIG. 9a, FIG. 9b and FIG. 9c illustrates a second embodiment of the grounding pin controlling structure.
Figure 9B:
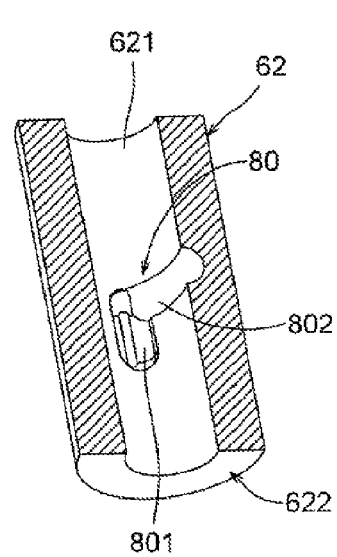
Figure 9C:
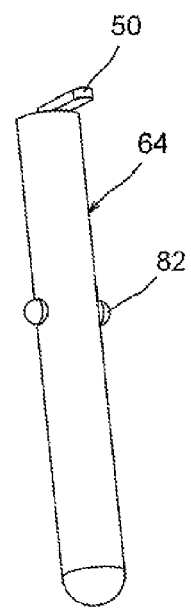

In second embodiment of the grounding pin controlling structure, as shown in FIG. 9a, the grounding pin controlling structure 60 includes a hollow cylinder 62 and a column 64 passing through the hollow cylinder 62. As shown in FIG. 9b, the hollow cylinder 62 has two opposite trenches 80 formed on an inner surface 621 of a side wall 622 of the hollow cylinder 62, wherein each trench 80 has a lengthwise ditch 801 and an upward-tilted ditch 802 connecting to a top end of the lengthwise ditch 801. Correspondingly, as shown in FIG. 9c, the column 64 has two opposite protrusions 82 on an outer surface of the column 64 and the protrusions 82 are respectively arranged within the opposite trenches 80, as shown in FIG. 9a to move along the lengthwise ditch 801 and the upward-tilted ditch 802. During the inspection of the EUV mask, the column 64 moves down in relative to the hollow cylinder 62 (shown in FIG. 7a), so that the grounding pin 50 contacts the reflective surface 16 of the EUV mask 10 (shown in FIG. 7a). After the inspection of the EUV mask 10, the column 64 moves up continuously in relative to the hollow cylinder 62, wherein the column 64 moves up straightly and then deflects as protrusions 82 moves along the lengthwise ditch 801 and then the upward-tilted ditch 802, so that the grounding pin 50 is far away from the EUV mask 10.

Figure 10A:
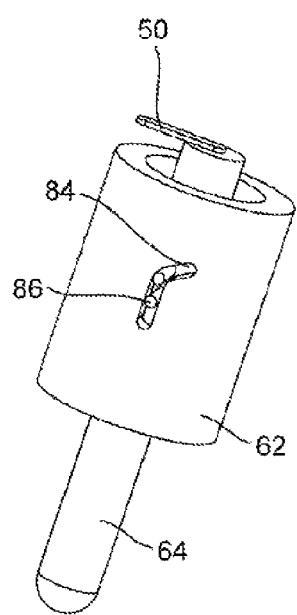
FIG. 10a, FIG. 10b and FIG. 10c illustrates a third embodiment of the grounding pin controlling structure.
Figure 10B:
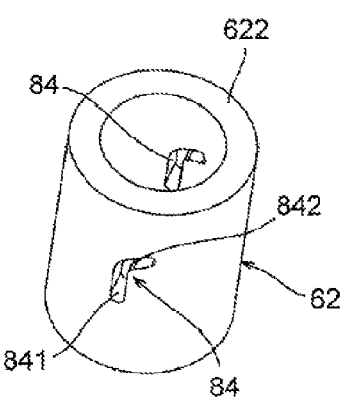
Figure 10C:
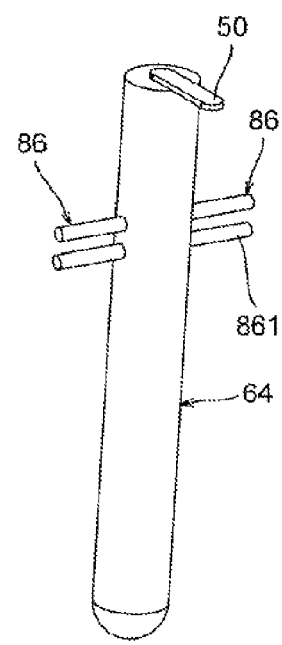

In third embodiment of the grounding pin controlling structure, as shown in FIG. 10a, the grounding pin controlling structure 60 includes a hollow cylinder 62 and a column 64 passing through the hollow cylinder 62. As shown in FIG. 10b, the hollow cylinder 62 has two opposite trenches 84 passing through a side wall 622 of the hollow cylinder 62, wherein each trench 84 has a lengthwise ditch 841 passing through the side wall 622 and a upward-tilted ditch 842 passing through the side wall 622 and connecting to a top end of the lengthwise ditch 841. Correspondingly, as shown in FIG. 10c, the column 64 has two opposite branch structures 86 including at least two horizontal rods 861 respectively, and the branch structures 86 are respectively arranged within the opposite trenches 84, as shown in FIG. 10a, to move along the lengthwise ditch 841 and the upward-tilted ditch 842. During the inspection of the EUV mask, the column 64 moves down in relative to the hollow cylinder 62 (shown in FIG. 7a), so that the grounding pin 50 contacts the reflective surface 16 of the EUV mask 10 (shown in FIG. 7a). After the inspection of the EUV mask 10, the column 64 moves up continuously in relative to the hollow cylinder 62, wherein the column 64 moves up straightly and then deflects as the branch structures 86 moves along the lengthwise ditch 841 and the upward-tilted ditch 842, so that the grounding pin 50 is far away the EUV mask 10.

Figure 11:
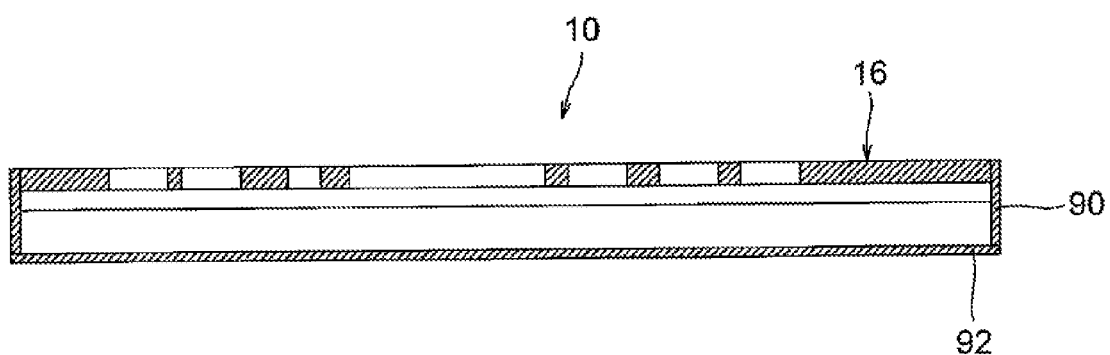
FIG. 11 illustrates a cross-sectional view of a configuration of another EUV mask.

In the foregoing embodiments, the grounding pin 50 is used to contact the reflective surface 16 which is formed on the top surface of the EUV mask 10. Nevertheless, the position that the grounding pin contacts with may be changed. As shown in FIG. 11, a first conductive layer 90 and a second conductive layer 92 may respectively be coated on the side of the EUV mask 10 and coated on the bottom surface, which is opposed to the reflective layer 16, of the EUV mask 10. The reflective surface 16, the first conductive layer 90 and the second conductive layer 92 are electrically connected, so that the foregoing grounding pin 50 may be used to contact the second conductive layer 92, so that charge on the reflective surface 16 of the EUV 10 mask is grounded through the first conductive layer 90 and the second conductive layer 92 to the grounding pin 50. The coated first conductive layer 90 and the second conductive layer 92 may be Al, Cr, Ti, alloy thereof, or non-metal such as carbon. The thickness of the first conductive layer 90 and the second conductive layer 92 may be 0.001 um to 1 mm.

Figure 12A:
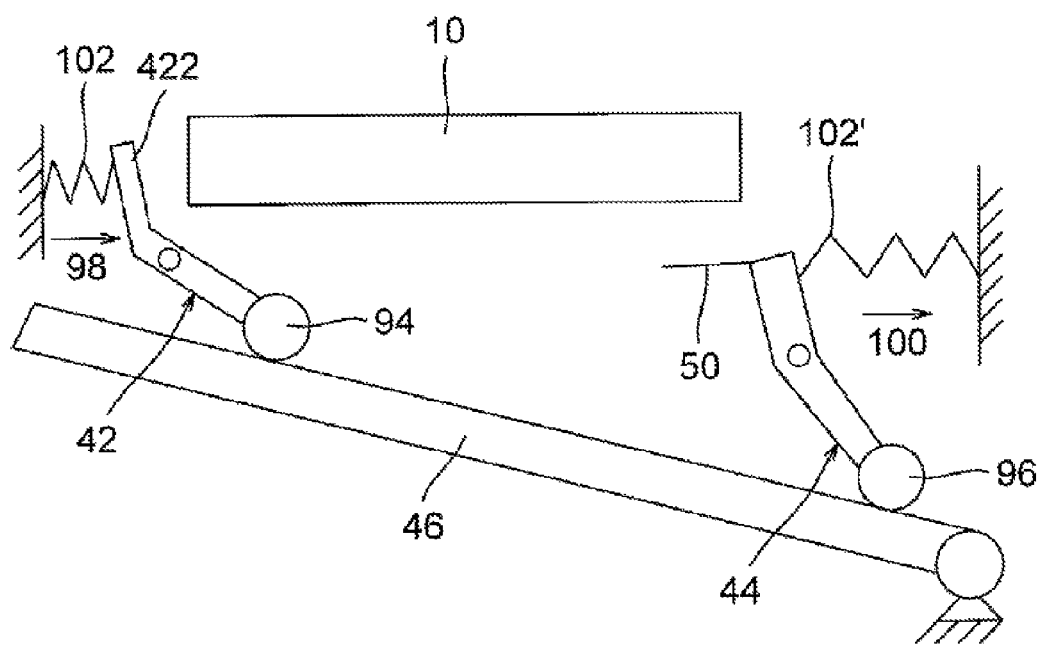
FIG. 12a and FIG. 12b illustrate the diagrams about the working status of the EUV mask and the grounding pin in accordance with the fourth embodiment of the present invention.
Figure 12B:
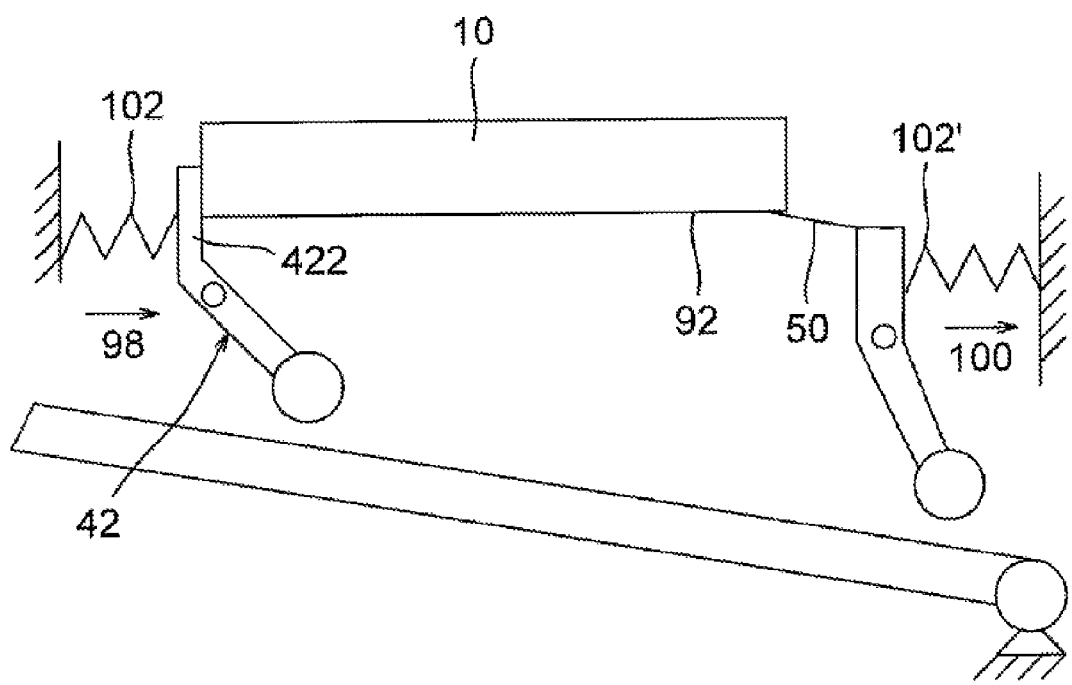

Continuing the above description, the drive mechanism of the gripper unit described in the second embodiment of the present invention may be applied to the EUV mask with the first conductive layer and the second conductive layer. As shown in FIG. 12a, when the reciprocating member 46 works to make the third rolling member 94 to move substantially along the third direction 98 and the fourth rolling member 96 move substantially along the fourth direction 100, the head portion 422 of the gripper unit 42 moves toward the opposite direction of the third direction 98 and the grounding pin 50 moves toward the opposite direction of the fourth direction 100 so that the head portion 422 and the grounding pin 50 are led away from the EUV mask 10. As shown in FIG. 12b, when the reciprocating member 46 works to leave from the third rolling member 94 and the fourth rolling member 96, the head portion 422 of the gripper unit 42 moves toward the third direction 98 by means of the third force of the third resilient member 102 and an upper portion of the arm structure 44 moves toward the fourth direction 100 by means of the fourth force of the fourth resilient member 102' so that the head portion 422 is therefore led toward the edge of the EUV mask 10 and in the end to abut against the EUV mask 10, and the grounding pin 50 contacts the second conductive layer 92 of the EUV mask 10 to discharge the charge on the reflective surface 16 of the EUV mask 10.

Figure 13A:
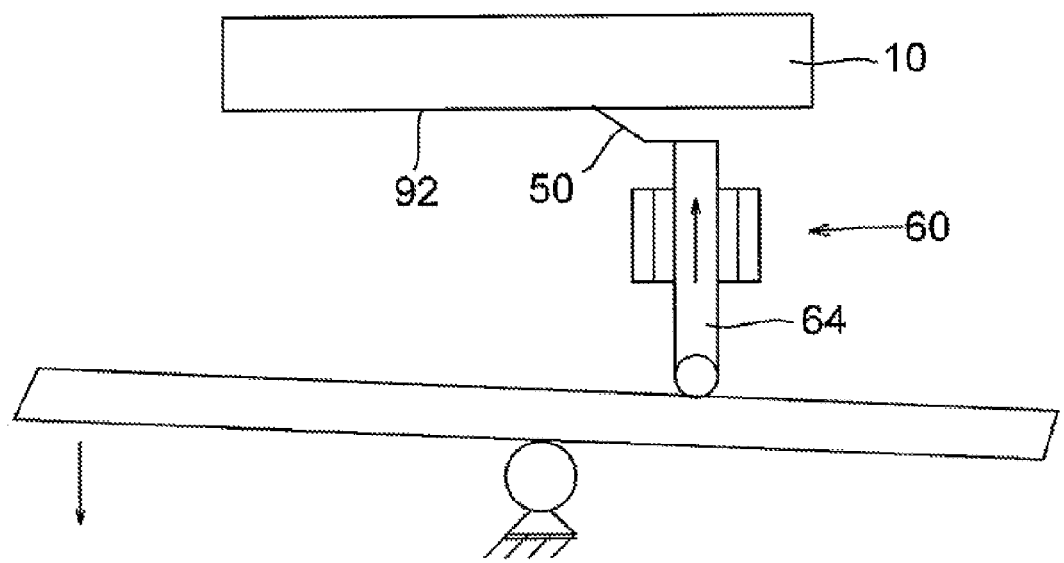
FIG. 13a and FIG. 13b illustrate the diagrams about the working status of the EUV mask and the grounding pin in accordance with the fifth embodiment of the present invention.
Figure 13B:
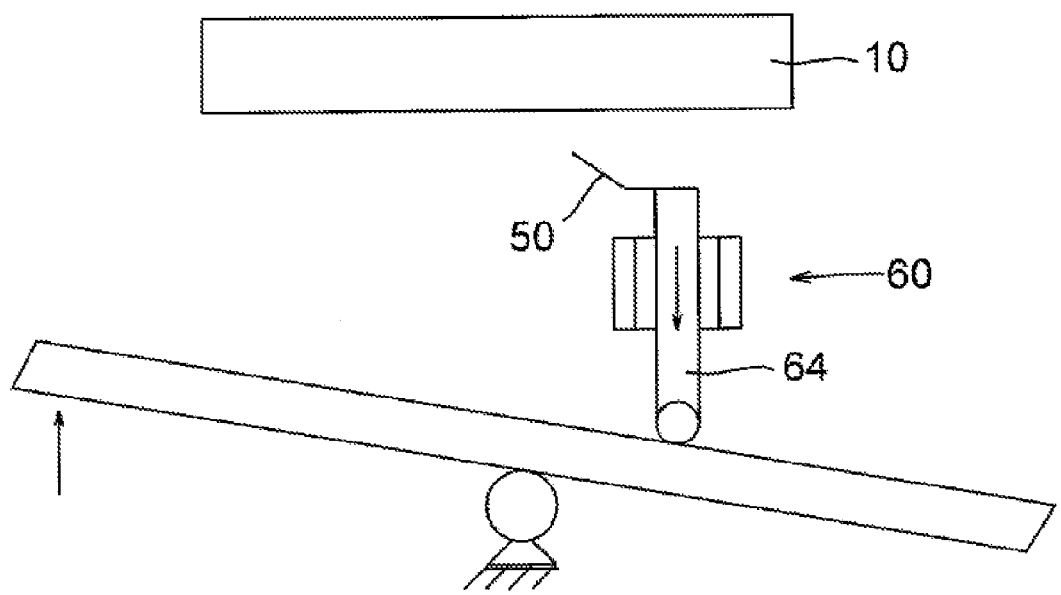

On the other hand, the grounding pin controlling structure 60 described in third embodiment of the present invention may also be applied to the EUV mask 10 with the first conductive layer 90 and the second conductive layer 92 thereon. As shown in FIG. 13a, during the inspection of the EUV mask 10, the column 64 moves up and the grounding pin 50 contacts the second conductive layer 92 of the EUV mask 10. After the inspection of the EUV mask 10, as shown in FIG. 13b, the column 64 moves down and the grounding pin 50 is far away from the EUV mask 10. The embodiments of the grounding pin controlling structure 60 are described above, and unnecessary details would not be given here.

Figure 14:
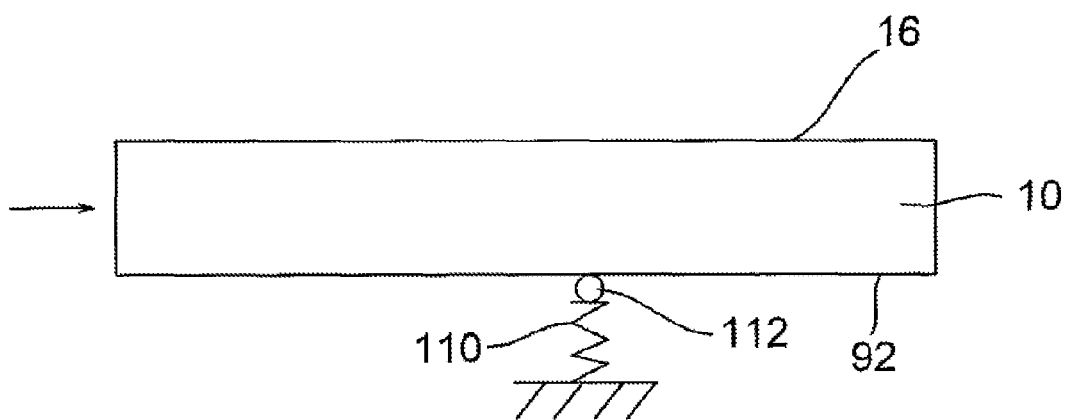
FIG. 14 illustrates the diagrams about the working status of the EUV mask and the grounding pin in accordance with the sixth embodiment of the present invention.

Furthermore, as shown in FIG. 14, the grounding pin may be a spring 110 with a trigger 112 on the top end of the spring 110, and the bottom end of the spring 110 is grounded. When the EUV mask 10 moves to be inspected, the second conductive layer 92 of the EUV mask 10 may contact with the trigger 112 by the weight of the EUV mask 10 to discharge the charge on the reflective surface 16 of the EUV mask 10.

Figure 15A:
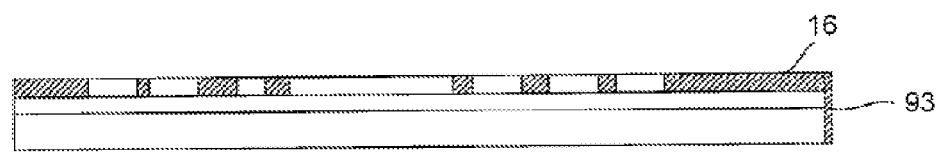
FIG. 15a and FIG. 15b respectively illustrates a cross-sectional view and a vertical view of a configuration of another EUV mask.
Figure 15B:
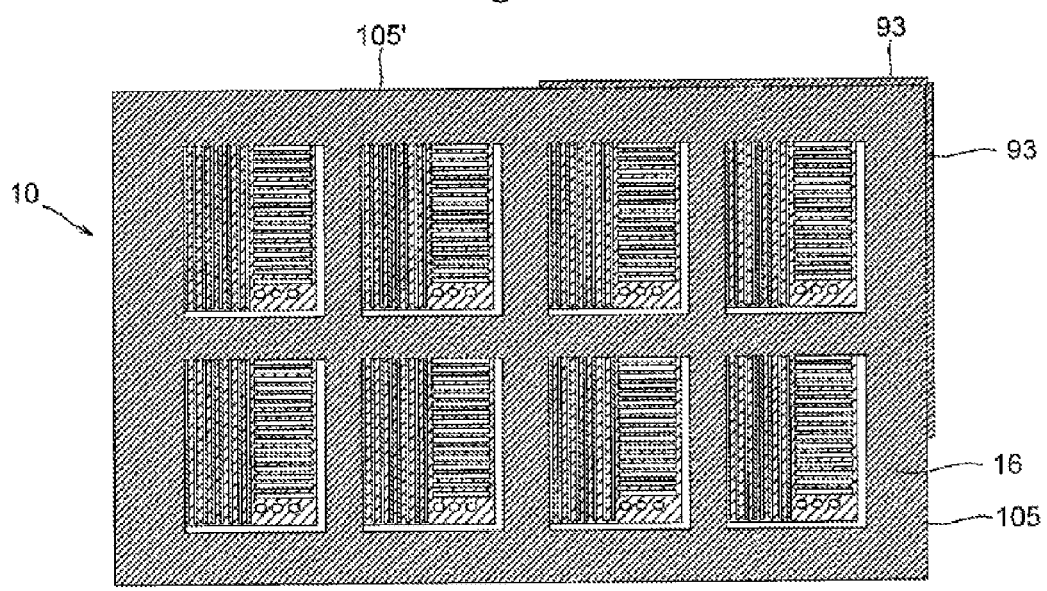
Figure 16:
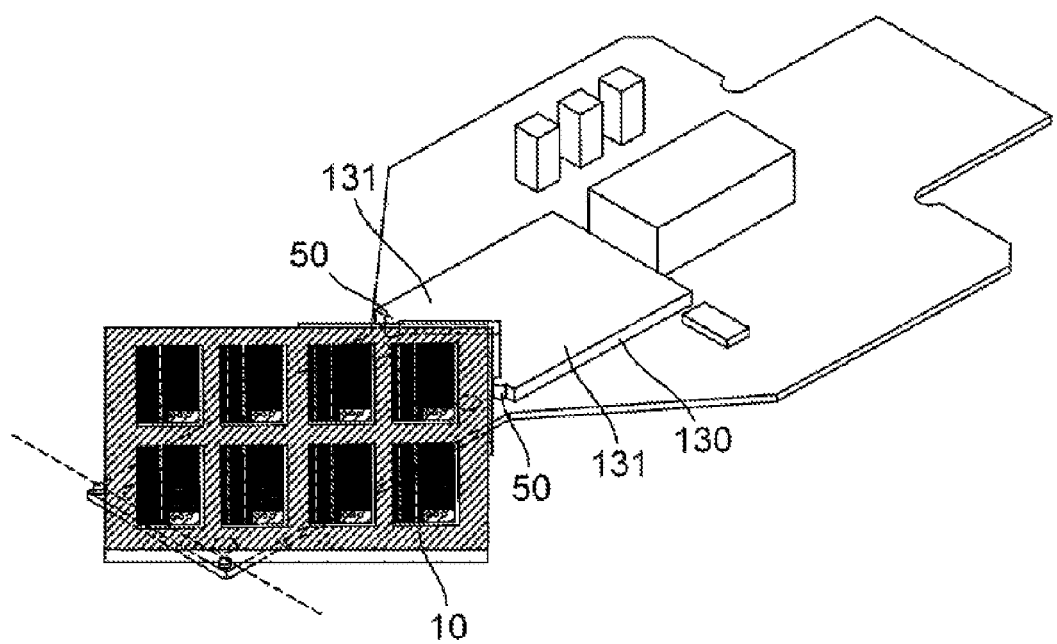
FIG. 16 illustrates a diagram of a conductive holder clamping the EUV mask in accordance with another embodiment of the present invention.

In another embodiment, the grounding pin is used to contact at least one conductive layer on one side of the EUV mask. As shown in FIG. 15a and FIG. 15b, a conductive layer 93 is formed on one corner of the EUV mask 10, the two adjacent side walls 105, 105', accordingly, and the conductive layer 93 is electrically connected to the reflective surface 16 of the EUV mask 10. The structure for discharging EUV mask includes a conductive holder 130 with the grounding pin 50, as shown in FIG. 16, to clamp the corner of the EUV mask 10, so that the grounding pin 50 may contact with the conductive layer 93. Refer to FIG. 16, two grounding pins 50 are respectively formed on a pair of opposite clamp sections 131 of the conductive holder 130, so that the two grounding pins 50 may contact the conductive layer 13 at two adjacent side walls 105, 105' of the EUV mask 10.

Figure 17:
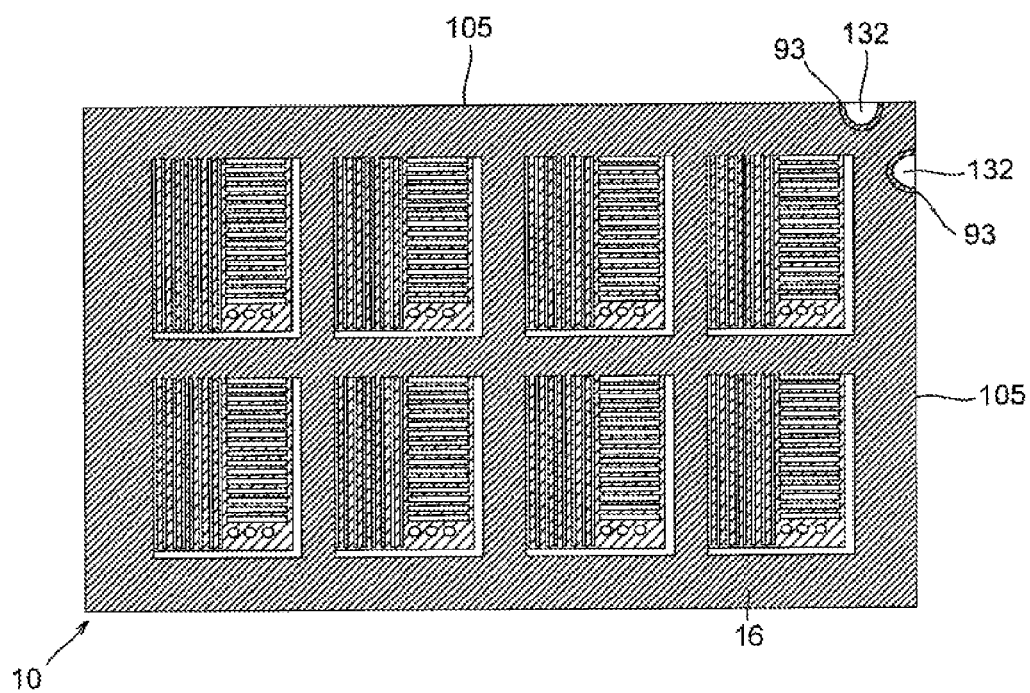
FIG. 17 illustrates a vertical view of a configuration of another EUV mask.

Further, as shown in FIG. 17, two trenches 132 or notches are respectively formed on two adjacent side walls 105, 105' of the EUV mask 10, and a conductive layer 93 formed on the trenches 132 or the notches is electrically connected to the reflective surface 16 of the EUV mask 10. Here, the profile of the trenches 132 or notches may correspond to the grounding pins 50 arranged on the conductive holder 130 as shown in FIG. 16, so that the grounding pin 50 may closely contact the conductive layer 93.

Figure 18:
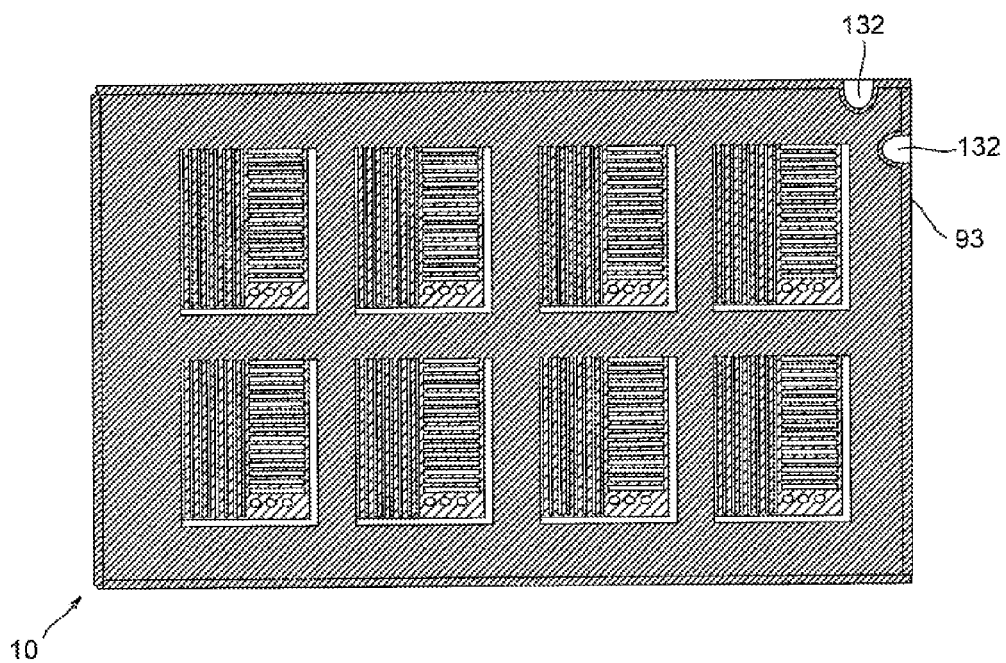
FIG. 18 illustrates a vertical view of a configuration of another EUV mask.

Furthermore, as shown in FIG. 18, the foregoing conductive layer 93 may be formed on the whole side wall, including the trenches 132 or the notches walls, of the EUV mask 10, so that the grounding pin 50 may contact with the conductive layer 93 conveniently. The coated conductive layer 93 may be Al, Cr, Ti, alloy thereof, or non-metal such as carbon. The thickness of the conductive layer 93 may be 0.001 um to 1 mm.

FIG. 19 is a flow chart illustrating a method for inspecting an EUV mask by using a charged particle beam according to an embodiment of the present invention. In step of S110, a grounding pin slightly contacts to the EUV mask while the EUV mask is positioned. Here, the grounding pin can contact the reflective surface, backside surface, or sidewall surface of the EUV mask to achieve a discharging effect. In step of S120, a stage, for supporting the EUV mask, is moved continuously, and the reflective surface of the EUV mask is scanned by using a charged particle beam simultaneously. Furthermore, the moving direction of the stage is perpendicular to the scanning direction of the charged particle beam. The charged particle beam, in one embodiment, is electron beam. In step of S130, signal electrons emanated from the reflective surface of the EUV mask can be received by a detector to form an imaging. Here, the signal electrons can be secondary electrons or backscattered electrons.

Figure 20:
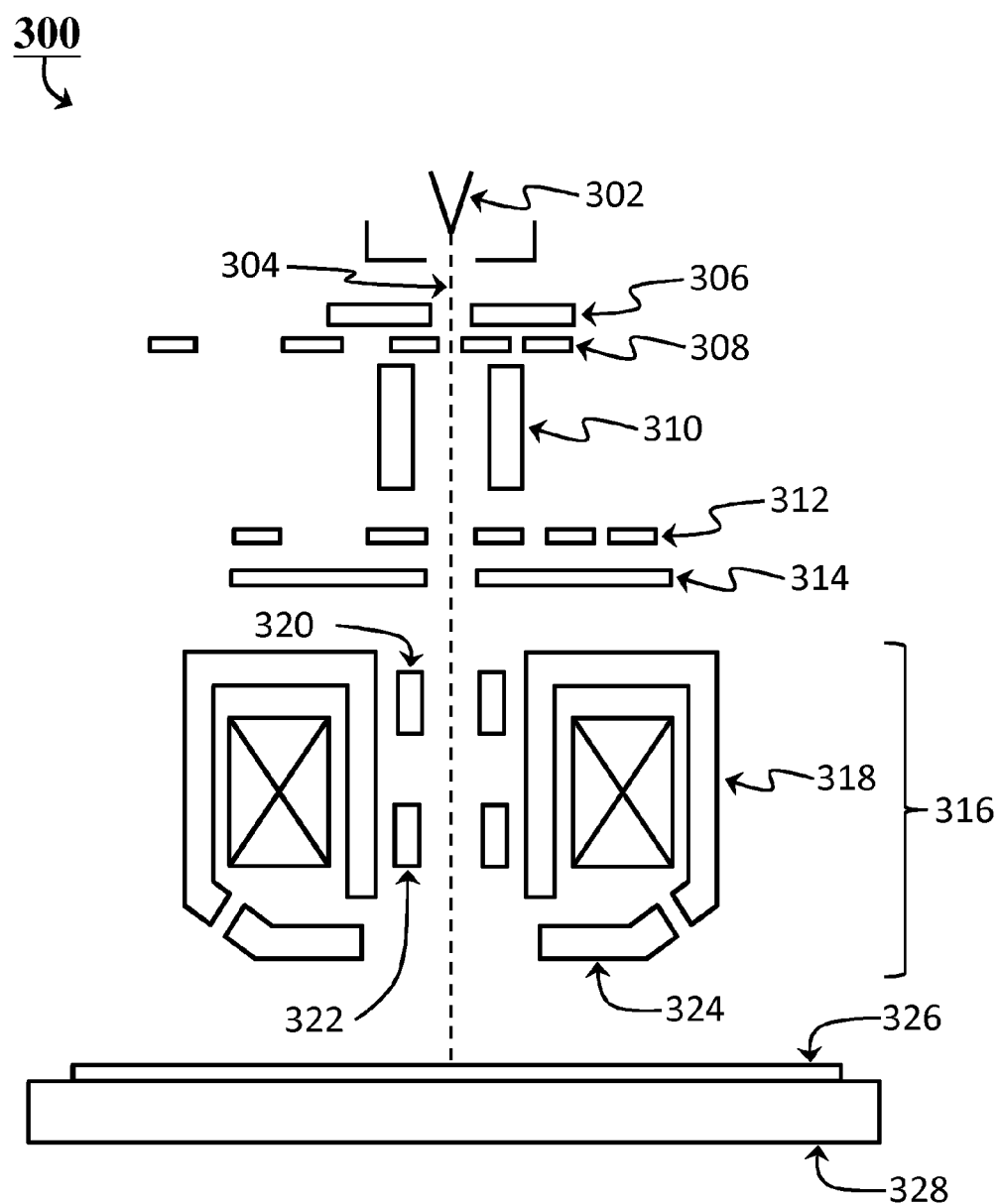
FIG. 20 shows an embodiment of a low voltage scanning electron microscope.

FIG. 20 shows a low voltage scanning electron microscope (LVSEM) used to inspect a EUV mask. In this figure, an objective lens can be a SORIL optical system.

In this embodiment of the scanning electron microscope 300, the electron beam 304 emitted from a cathode 302 is accelerated by an anode 306 voltage, passes through a gun aperture 308, a condenser lens 310, a beam limit aperture 312 and a SORIL system 316, and then impinges onto a specimen surface 326 supported by a stage 328.

When a fixed negative potential Vc and a potential Va, which is enough higher than Vc, are respectively applied to the field emission cathode 302 and the anode 306, the electron beam 304 is emanated from the cathode 302 along an optical axis. The emanated electrons are firstly accelerated in the space between the cathode 302 and anode 306, and then decelerated (accelerated or remain even speed in some cases) in the space between the anode 306 and a terminal electrode at ground potential.

Because the gun aperture 308 is closer to the electron source, the electron beam 304 with larger polar angles can be cut off by the gun aperture 306, and trimmed down to a specific current value. It can also be earlier to prevent from the Coulomb interaction of the electron beam. Then the electron beam 304 passes the condenser lens 310 and the beam limit aperture 312. The condenser lens 310 can weakly condense the electron beam 304. The beam limit aperture 312 can determine the amount of the electron beam 304 to a desired beam current on the specimen 326, and allow entering the objective lens system 316 with a fixed energy, a fixed brightness and a fixed beam current.

The SORIL system 316 includes an objective lens 318, deflectors 320 and 322 which are located inside the objective lens 318, and a control electrode 324. The objective lens 318 can be an immersion electrostatic objective lens, an immersion magnetic objective lens, or an electromagnetic compound objective lens. In the embodiment, the immersion magnetic objective lens 318 is more preferred. The immersion magnetic objective lens 318 can focus the electron beam 304 into a small spot which is used to scan the studied specimen 326. Because focusing the electron beam 304 is mainly accomplished by the magnetic objective lens 318, the aberrations of the beam spot mostly come from the spherical aberration and the chromatic aberration of the magnetic objective lens 318. The purpose of the immersion magnetic objective lens 318 is to generate a magnetic field with a large component perpendicular to the Z-axis for converging lens action above the specimen 326 and to have the magnetic field substantially parallel to the Z-axis at the specimen 326. Accordingly, the specimen 326 can be immersed in the magnetic field of the lens.

The deflection units 320 and 322 in the SORIL system 316 can be equipped with electrostatic multi-pole deflectors or magnetic multi-pole deflectors. The embodiment is more preferred the electrostatic multi-pole deflectors because the magnetic multi-pole deflectors would produce magnetic hysteresis phenomenon on deflecting the electron beam 304 during operation. Therefore, it would affect the scanning speed. The electron beam 304 can be deflected by the deflection units 320 and 322 which can generate a small deflection field, or can work together with the control electrode 324 to increase the size of the deflection field, so that the specimen 326 can be scanned by the focused beam. Furthermore, the deflection units are designed to minimize the introduction of aberrations into the beam when deflecting the electron beam. In accordance with the embodiment, the deflection units 320 and 322 are dedicated to produce a more rapid scanning movement of the electron beam 304 to cover a suspected region, and it can enhance the throughput of the imaging.

The control electrode 324 is made of electrical conduction material. The control electrode 324 is shaped and positioned to be an extension of outer polepiece of the magnetic objective lens 318 towards optical axis. The control electrode 324, on one hand, is set to a voltage Vce to control the electrical field on the specimen surface 326 lower than the predetermined value, which ensures on micro-arcing on the specimen surface 326. On the other hand, the voltage Vce of the control electrode 324 can be dynamically adjusted to compensate the image defocus due to electric drifting.

Since an imaging with better quality can be obtained through the electron beam 304 impinging on the specimen surface 326, the system needs to make every component's applied voltage and excitation current synchronize. Any electric drifting on these components will cause the spot size of the electron beam 304 varied and defocus of the image. The control electrode 324 can be dynamically performing micro-focusing while the image is defocused. The control electrode 324 can increase the magnetic field strength of the SORIL system 316 under a same excitation. Placing the control electrode 324 in the retarding field gives the control electrode 324 a great deal of influence over the trajectory of the electron beam 304 because the electron beam 304 has been reduced to a lower landing energy than the deflection units 320 and 322, and it is nearest the landing point of the electron beam on the specimen 326. Furthermore, because of its proximity to the specimen 326, it can help to accurately position the electron beam 304 over a selected area of the specimen 326 prior to the rapid scan of the area, and improve the size of the deflection field over the specimen 326.

The SORIL system 316 adopted in the embodiment is preferred because it can reduce the off-axis chromatic and spherical aberrations greatly in scanning imaging, and is better at extending its magnetic field below the lens aperture and through the specimen 326 to increase the field of view.

To reveal a stereo imaging of the specimen surface 326 with better imagine quality, the embodiment of the present invention can adopt the multi-channel detector 314 to collect the signal electrons during the scanning operation. The signal electrons, including the secondary electrons or the backscattered electrons, emanated from the different sides or features of the specimen surface 326 can be collected by different channels. Therefore, the signal electrons from the different emanated directions can generate a stereo image in combination, and finally ensure a topography analysis of the defects of interest regions.

The specimen 326 on the specimen stage 328 is charged with a negative voltage to create a retarding field Er; that is, a field in the opposite direction to the accelerating field Ea to reduce the energy of the electron beam prior to impact with the specimen 326, and avoid great damage of the specimen surface. Furthermore, the retarding field can make the electron beam 304 land on the specimen surface with a lower landing energy.

Figure 21:
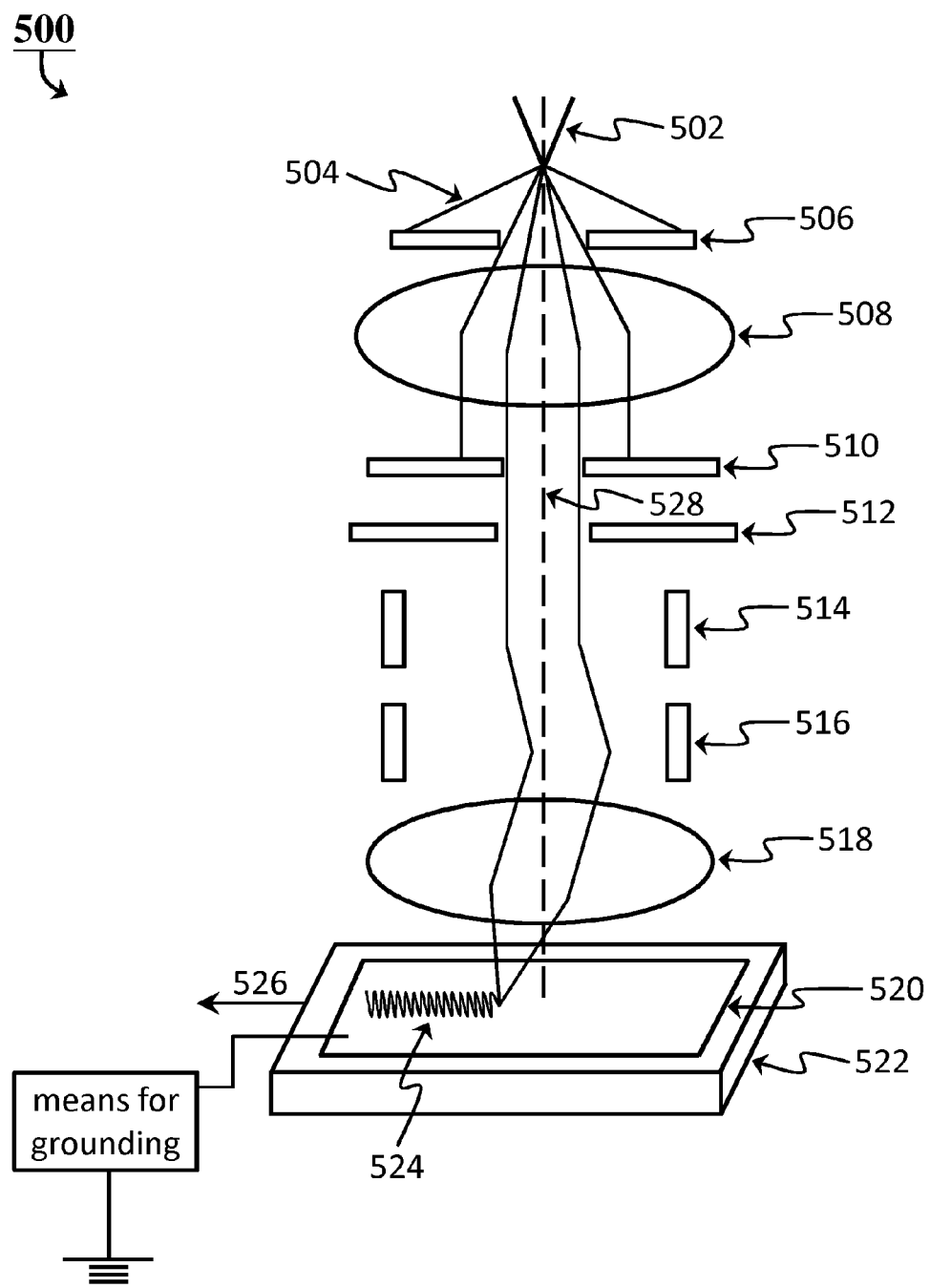
FIG. 21 shows a schematic diagram of a structure for an electron beam inspection system processing continuous scanning on an EUV mask in accordance with one embodiment of the present invention.

FIG. 21 shows a schematic diagram of a structure 500 for an electron beam inspection system processing continuous scanning on a EUV mask. The electron beam inspection system adopts the LVSEM disclosed in the FIG. 20, and is expressed in a simplified manner.

A stage 522 on the inspecting system is used for supporting the EUV mask 520. The reflective surface of the EUV mask 520 is continuously scanned by using the electron beam 504 when the stage 522 moves continuously at the same time. The stage 522 can move along the direction 526 and the surface of EUV mask 520 can be scanned by the electron beam 504 under the control of the first deflector 514 and the second deflector 516. The moving direction of the stage is perpendicular to the scanning direction of the electron beam. When the EUV mask 520 is inspected by using the electron beam 504, it should be grounded simultaneously.

And the signal electrons emanated from the surface of the EUV mask 520 would be received by a detector 512.

No matter the grounding pin is contacted with the reflective surface, the bottom conductive layer or the side conductive layer, the present invention provides a structure to discharge the EUV mask during inspection by an E-beam inspection tool, so that non accumulated charging is on the EUV mask during E-beam inspecting to enhance the inspection quality.

In the present invention, when applying the foregoing structure to discharge the EUV mask to an electron beam inspection system, the electron beam inspection system for inspecting an EUV mask includes: an electron gun for providing electron beam; a lens for focusing the electron beam on the EUV mask; a detector for receiving signal electrons emanating from the EUV mask; and means for discharging the EUV mask during the EUV mask is inspected; the reflective surface of the EUV mask on a continuous moving stage is scanned by using the electron beam simultaneously under the control of the first deflector and second deflector; the movement direction of the stage is perpendicular to the scanning direction of the electron beam. The inspection quality of the EUV mask is enhanced by using the electron beam inspection system because the accumulated charging on the EUV mask is grounded.

Although the present invention has been explained in relation to its preferred embodiment, it is to be understood that other modifications and variation can be made without departing the spirit and scope of the invention as hereafter claimed.

What is claimed is:

1. A method for inspecting an EUV mask by using a charged particle beam, wherein the EUV mask comprises a reflective surface, the charged particle beam is an electron beam, and the reflective surface comprises a patterned reflective surface area and a peripheral area, the method comprising:
   grounding the EUV mask via the peripheral area, wherein the peripheral area is electrically connected to the patterned reflective surface area;
   moving continuously a stage, wherein the stage is for supporting the EUV mask, and simultaneously scanning the patterned reflective surface area of the EUV mask by using the charged particle beam; and
   receiving signal electrons emanated from the patterned reflective surface area of the EUV mask;
   wherein, the stage's moving direction is perpendicular to a scanning direction of the electron beam, the EUV mask is inspected by a low voltage scanning electron microscope; and
   wherein, said step of grounding the EUV mask is performed by slightly contacting a grounding pin to a conductive layer on one side wall of the EUV mask, wherein a trench is formed in the side wall of the EUV mask.

2. The method for inspection an EUV mask by using a charged particle beam according to claim 1, wherein said conductive layer is coated within said trench.

3. A system for inspecting an EUV mask, wherein the EUV mask comprises a reflective surface, the charged particle beam is an electron beam, and the reflective surface comprises a patterned reflective surface area and a peripheral area, the system comprising:
   a source for providing an electron beam;
   an objective lens for focusing the electron beam on the patterned reflective surface area of the EUV mask;
   a detector for receiving signal electrons emanated from the patterned reflective surface area of the EUV mask;
   a stage for supporting the EUV mask; and
   means for grounding the EUV mask via the peripheral area, wherein the peripheral area is electrically connected to the patterned reflective surface area,
   wherein the patterned reflective surface area of the EUV mask is scanned by the electron beam when the stage moves continuously;
   wherein, the stage's moving direction is perpendicular to a scanning direction of the electron beam, the system is a low voltage scanning electron microscope; and
   wherein, said means for grounding the EUV mask includes a grounding pin contacting a conductive layer on one side wall of the EUV mask, wherein a trench is formed in the side wall of the EUV mask.

4. The system for inspecting an EUV mask according to claim 3, wherein said conductive layer is coated within said trench.

* * * * *